(12) United States Patent
Daniel et al.

(10) Patent No.: US 10,173,014 B2
(45) Date of Patent: Jan. 8, 2019

(54) CAP ASSEMBLY

(71) Applicant: Carebay Europe Ltd., Swatar (MT)

(72) Inventors: Mattias Daniel, Stockholm (SE);
Sebastian Karlsson, Sundbyberg (SE)

(73) Assignee: Carebay Europe Ltd, Sliema (MT)

( * ) Notice: Subject to any disclaimer, the term of this patent is extended or adjusted under 35 U.S.C. 154(b) by 942 days.

(21) Appl. No.: 14/391,957

(22) PCT Filed: Apr. 9, 2013

(86) PCT No.: PCT/EP2013/057342
§ 371 (c)(1),
(2) Date: Oct. 10, 2014

(87) PCT Pub. No.: WO2013/153045
PCT Pub. Date: Oct. 17, 2013

(65) Prior Publication Data
US 2015/0065961 A1 Mar. 5, 2015

Related U.S. Application Data

(60) Provisional application No. 61/622,256, filed on Apr. 10, 2012.

(30) Foreign Application Priority Data

Apr. 10, 2012 (SE) ........................ 1250359

(51) Int. Cl.
*A61M 5/32* (2006.01)
*A61M 39/20* (2006.01)
(52) U.S. Cl.
CPC .......... *A61M 5/3202* (2013.01); *A61M 5/321* (2013.01); *A61M 5/3213* (2013.01); *A61M 39/20* (2013.01)

(58) Field of Classification Search
CPC .... A61M 39/20; A61M 5/3202; A61M 5/321; A61M 5/3213
See application file for complete search history.

(56) References Cited

U.S. PATENT DOCUMENTS

| 3,835,862 A | 9/1974 | Villari | |
|---|---|---|---|
| 2009/0005735 A1* | 1/2009 | Wikner | A61M 5/20 604/131 |
| 2013/0035644 A1* | 2/2013 | Giambattista | A61M 5/2466 604/192 |

FOREIGN PATENT DOCUMENTS

| EP | 1466638 A2 | 10/2004 |
|---|---|---|
| WO | 2007/099044 A1 | 9/2007 |
| WO | 2011/126439 A1 | 10/2011 |

OTHER PUBLICATIONS

EPO, Int'l Search Report in PCT/EP2013/057342, dated Aug. 27, 2013.
EPO, Written Opinion in PCT/EP2013/057342, dated Aug. 27, 2010.

* cited by examiner

*Primary Examiner* — Brandy S Lee
(74) *Attorney, Agent, or Firm* — Piedmont Intellectual Property

(57) ABSTRACT

The present invention relates to a cap assembly 10 configured to be connectable to a suitable medicament delivery device having a distal and a proximal end. The cap assembly 10 according to the present invention comprises a removable outer 12 cap and a removable inner 16 cap movably connected in relation to each other. Further, said cap assembly is configured to allow said removable outer cap and said removable inner cap to be fixedly connectable to each other such that the removable outer cap is prevented of being movable with respect to the removable inner cap only when the medicament delivery device is held in a substantially (Continued)

vertical position such that both said removable outer cap and said removable inner cap can be removed from the cap assembly.

13 Claims, 10 Drawing Sheets

CAP ASSEMBLY

TECHNICAL AREA

The present invention relates to a cap assembly for a medicament delivery device and in particular a cap assembly for injection needle protection comprising an outer and an inner cap, having enhanced safety aspects.

BACKGROUND OF INVENTION

For many injection devices intended for self-administration of medicament, it is often desirable that the device is as complete as possible, i.e. that the number of operations or assembly steps needed in order to make the device ready to deliver a dose of medicament is minimized.

One solution for keeping a medicament delivery device as pre-assembled as possible is to deliver the medicament delivery device with a delivery member, such as a needle, pre-attached. This solution often causes the rear end of the needle to protrude into the interior of the container, which could be a drawback if the medicament reacts with the material of the delivery member when exposed for a period of time. In that respect it would be desirable to have the rear part of the delivery member outside the container until the delivery is to be performed.

On the other hand, the front part of the delivery member has to be protected before use in order to prevent unintentional needle sticks and in order to keep the needle clean. The front end of the delivery member is therefore often arranged with a sheath and/or a cap that has to be removed beforehand.

In order to accomplish the above in a simple and effective way, the applicant has developed a cap assembly that comprises a retainer member connectable to a medicament container holder of a medicament delivery device. The cap assembly further comprises a hub coaxially movable within the retainer member where the hub comprises a needle having a proximal end and a distal end. An inner cap is interactively connected to the hub and the retainer member. The engagement between the outer cap and the inner cap and between the inner cap and the retainer member is configured such that removal of the outer cap causes the hub to move distally such that the distal end of the needle penetrates the proximal end of the medicament container.

For some types of medicament to be delivered, that are contained in a medicament container placed inside the medicament delivery device, there is a tendency that pressure can build up inside the container, which pressure could be considerable. When a cap assembly like the one described above then is operated for removing it and the distal end of the needle penetrates the medicament container, the over-pressure is relieved through the needle.

If the device is held correctly with the proximal end of the injection needle pointing substantially vertical upwards, then mostly air will be relieved through the needle during de-aeration. However, if the device is tilted and is held more horizontally, then amounts of medicament will be expelled through the needle when the over-pressure is relieved.

This is a drawback in many ways. If the medicament container comprises a certain prescribed dose volume to be delivered to a patient, then unintentional expelling of a volume during removal of the cap assembly will lead to an inferior dose quantity being delivered during the subsequent injection. If a multi-dose container is used, then the last dose to be delivered will be of inferior volume. This may be serious for drugs requiring certain rather specific dose volumes in order to give adequate treatment. Also, the mere uncontrolled expelling of a drug volume into the environment is a hazzle and an inconvenience.

Some solutions have been presented for ascertaining that medicament delivery devices are held in a proper position during certain handling steps. For example, the document WO 2007/099044 discloses a medicament delivery device, which is arranged to handle a multi-chamber medicament container. In order to ascertain that the device is held in the proper vertical position during the priming of the multi-chamber container after a mixing operation, a direction sensitive mechanical solution is presented, which can comprise a ball that may be moved from an engagement position, enabling priming, to a disengagement position where no priming may be performed. In the engagement position, it is possible to manually push a priming sleeve such that a pre-tensioned plunger rod is released a certain predetermined distance such that the medicament container is primed by expelling entrapped air.

This solution is rather complicated since the design is built into the device, adding costly features to the design. Also WO 2007/099044 only deals with the situation during priming after mixing of a multi-chamber container. The solution comprises a number of features and interacting components. Further, the document does not deal with the situation when the inner of a medicament container is suddenly in communication with the surrounding by a penetrating needle during removal of the cap assembly.

BRIEF DESCRIPTION OF INVENTION

In order to overcome one or several of the above-mentioned problems, a cap assembly for a medicament delivery device according to independent claim 1 is provided.

Further aspects, improvements and variations are disclosed in the dependent claims, the figures and the description.

In the present application, when the term "distal" is used, this refers to the direction pointing away from the dose delivery site. When the term "distal part/end" is used, this refers to the part/end of the delivery device, or the parts/ends of the members thereof, which is/are located furthest away from the dose delivery site. Correspondingly, when the term "proximal" is used, this refers to the direction pointing to the dose delivery site. When the term "proximal part/end" is used, this refers to the part/end of the delivery device, or the parts/ends of the members thereof, which is/are located closest to the dose delivery site.

According to a main aspect of the invention, it relates to a cap assembly configured to be connectable to a medicament delivery device having a distal and a proximal end, said cap assembly comprises a removable outer cap and a removable inner cap movably connected in relation to each other wherein said cap assembly is configured to allow said removable outer cap and said removable inner cap to be fixedly connectable to each other such that the removable outer cap is prevented of being movable with respect to the removable inner cap only when the medicament delivery device is held in a substantially vertical position such that both said removable outer cap and said removable inner cap can be removed from the cap assembly.

According to a further aspect of the invention, the removable outer cap and the removable inner cap are movably connected to in relation to each other such that the removable outer cap is prevented of being longitudinally displaceable but rotatable with respect to the removable inner cap and wherein the cap assembly is configured to allow said removable outer cap and said removable inner cap to be fixedly connectable to each other such that the removable outer cap is prevented of being rotatable with respect to the removable inner cap only when the medicament delivery device is held in a substantially vertical position such that both said removable outer cap and said removable inner cap can be removed from the cap assembly.

According to another aspect of the invention, said cap assembly comprises a retainer member connectable to the medicament container holder so as to provide a fixed connection between the cap assembly and the medicament delivery device. The cap assembly further comprises a shield front which is also connectable to the medicament delivery device, preferably to a movable shield sleeve of the medicament delivery device.

According to yet another aspect of the invention, the cap assembly is arranged with a hub comprising a needle having a proximal end and a distal end, where the hub may be coaxially movable within the retainer member. The removable inner cap is interactively connected to the hub and to the retainer member, as well as the removable outer cap is coaxially arranged and connectable to the inner cap.

According to a preferable solution of the invention, said cap assembly further comprises a biased clutch sleeve coaxially and movable arranged between said inner and outer caps and being releasibly connectable to both said inner and outer caps; a biased outer cap locking means coaxially arranged between the outer cap and the clutch sleeve and movable between a disconnected position in which the biased outer cap locking means is disconnected from both the outer cap and the clutch sleeve and a connected position in which the biased outer cap locking means is connected to both the outer cap and the clutch sleeve; and a clutch sleeve locking member arranged between the clutch sleeve and the outer cap and movable between a blocking position in which the clutch sleeve locking member is connected to both the clutch sleeve and the outer cap for preventing the clutch sleeve to be moved in relation to said inner and outer caps and an unblocking position in which the clutch sleeve locking member is disconnected from both the clutch sleeve and the outer cap for allowing the clutch sleeve to be moved in relation to the inner and outer caps. Further, the clutch sleeve, the outer cap, and the clutch sleeve locking member are configured such that clutch sleeve locking member is movable from the unblocking to the blocking position only when the medicament delivery device is held in a substantially vertical position.

According to a further aspect of the invention, the removable outer cap is configured to be biased disconnected from the clutch sleeve such that the outer cap is rotatable with respect to the clutch sleeve only when the biased outer cap locking means is in the disconnected position and the clutch sleeve locking member is either in the blocking or unblocking position.

According to another aspect of the invention, the removable outer cap is configured to be connected to the clutch sleeve such that the outer cap and the clutch sleeve are rotatable with respect to the inner cap only and the clutch sleeve is longitudinally displaceable in relation to the inner cap when the biased outer cap locking means is in the connected position and the clutch sleeve locking member is in the unblocking position.

According to yet another aspect of the invention, the biased clutch sleeve and the inner cap are configured to be connected to each other such that the clutch sleeve is neither rotatable nor longitudinally displaceable with respect to the inner cap only when the clutch sleeve locking member is in the blocking position and the biased outer cap locking means is in the connected position.

According to a further aspect of the invention, the outer and inner caps are configured to be connectable to each other through the clutch sleeve such that a movement of the outer cap can be transferred to the inner cap only when the clutch sleeve locking member is in the blocking position and the biased outer cap locking means is in the connected position.

This solution provides the removal of both the outer and the inner when the clutch sleeve locking member is in the blocking position and the biased outer cap locking means is in the connected position. On the other hand, when the clutch sleeve locking member is in the unblocking position and the biased outer cap locking means is in the connected position or when the clutch sleeve locking member is in the blocking position and the biased outer cap locking means is in the disconnected position or when the clutch sleeve locking member is in the unblocking position and the biased outer cap locking means is in the disconnected position, rotation of the outer cap will not cause rotation of the inner cap and thus no removal of the cap assembly from the medicament delivery device is achieved.

According to a favourable solution, the outer cap comprises a proximal end wall having a central opening in which a proximal end of the inner cap is positioned such that the outer cap is prevented of being longitudinally displaceable but rotatable with respect to the inner cap. The outer cap further comprises a coaxial tubular blocking member which extends longitudinally a certain length from the proximal end wall towards the distal end of the device and through which the proximal part of the inner cap extends. The biased clutch sleeve comprises at its proximal end a cup shaped member having a central opening through which a proximal part of the inner cap extends. A resilient member is arranged surrounding the coaxial tubular blocking member and between a circumferential ledge surface of the cup shaped member and a support surface(s) on the inner surface of the outer cap for biasing the clutch sleeve. The clutch sleeve locking member is movable arranged in the cup shaped member and the clutch sleeve locking member is a rolling member. The biased clutch sleeve comprises a camming surface and the inner cap comprises a corresponding camming surface, said camming surfaces are configured to interact with each other, wherein, when said clutch sleeve locking member is in the blocking position and the biased outer cap locking means is in the connected position said camming surfaces are rotationally locked whereby rotation of said outer cap causes rotation of said inner cap, and wherein, when said clutch sleeve locking member is in the unblocking position and the biased outer cap locking means is in the connected position said camming surfaces are rotationally non-locked whereby rotation of said outer cap causes a rotation and a longitudinal displacement of said biased clutch sleeve in relation to the inner cap.

The clutch sleeve locking member is preferably a ball. It may however be any other type of geometrical shape that is capable of moving in and out of engagement. An advantage is that the surface enables the rolling member to move radially in 360 degrees directions.

In one embodiment of the invention, the clutch mechanism may further comprise a clutch sleeve arranged operable between said outer cap and said inner cap, wherein said surface is arranged to said clutch sleeve.

Preferably said camming surfaces comprise cooperating inclined surfaces. The inclined surfaces may have the shape teeth in a ratchet, but also other shapes are feasible in allowing the desired function.

As a safety feature the biased outer cap locking means is connected to or integral with a clutch biasing means. Said clutch biasing means is a resilient member, preferably integrally to the biased outer cap locking means. The function of the clutch biasing means is to return the biased outer cap locking means to the disconnected position if the cap assembly has been exposed to a sudden external force, such as if e.g. the medicament delivery device was dropped with its proximal end on a hard surface.

These and other aspects of, and advantages with, the present invention will become apparent from the following detailed description of the invention and from the accompanying drawings.

BRIEF DESCRIPTION OF DRAWINGS

In the following detailed description of the invention, reference will be made to the accompanying drawings, of which

DETAILED DESCRIPTION OF THE INVENTION

Figure 1:
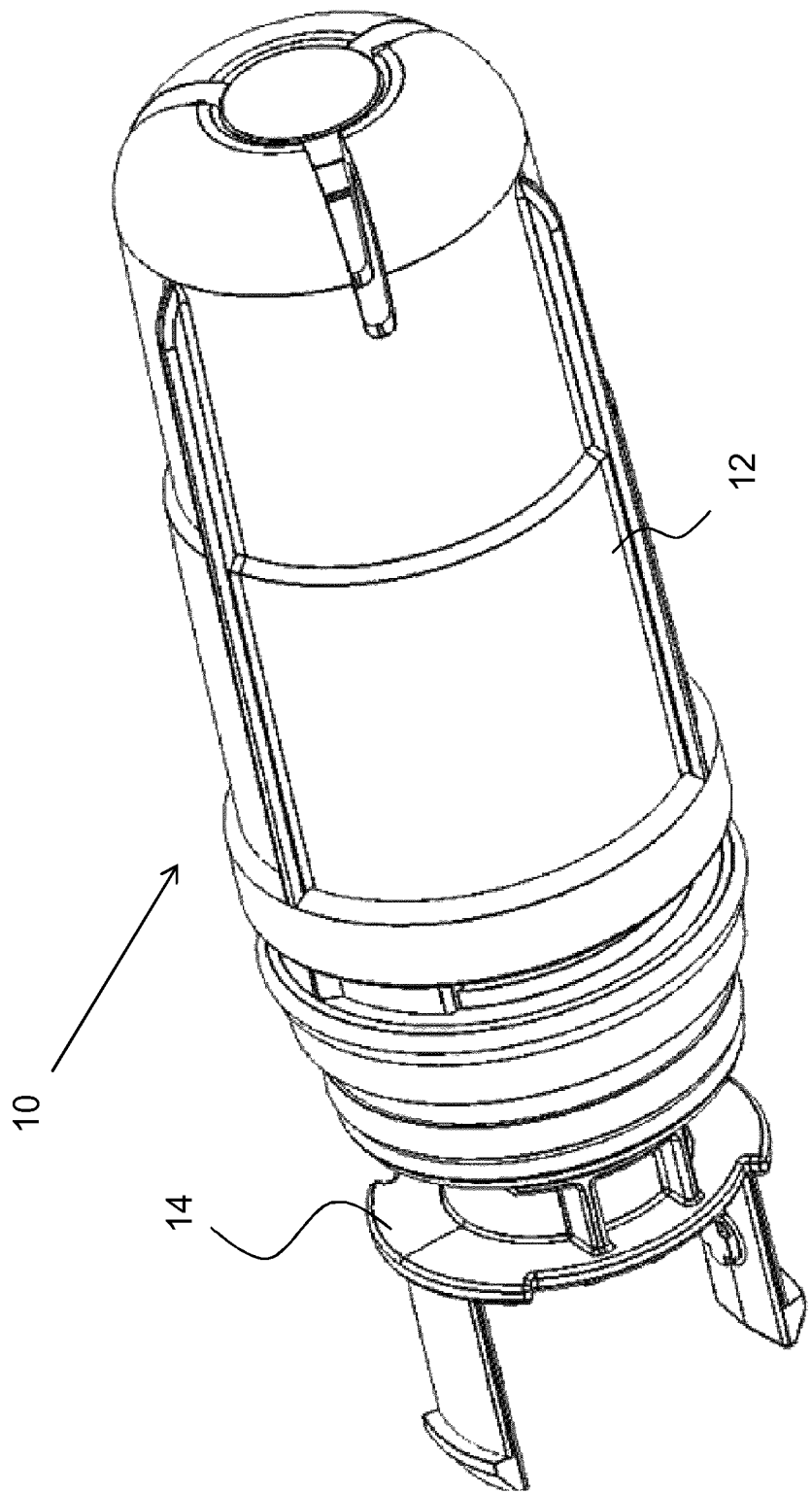
FIG. 1 shows a perspective view of a non-limiting example of a cap assembly comprising the present invention, which may be used with a medicament delivery device.
Figure 2:
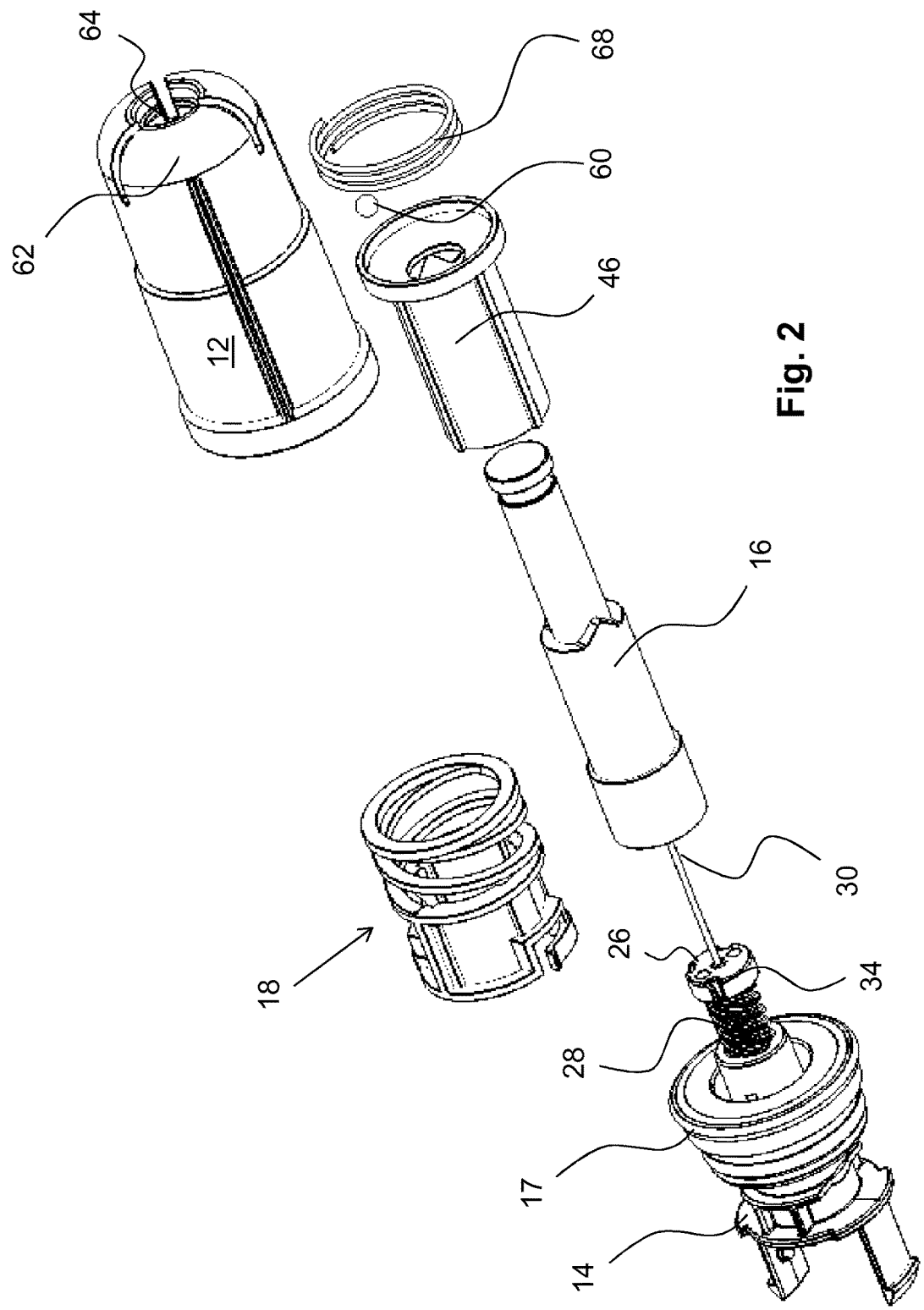
FIG. 2 shows an exploded view of the non-limiting example of the cap assembly of FIG. 1.

FIGS. 1 and 2 show a cap assembly 10 according to the present invention is configured to be connectable to a suitable medicament delivery device having a distal and a proximal end. The cap assembly 10 according to the present invention comprises a removable outer 12 cap and a removable inner 16 cap movably connected in relation to each other. Further, said cap assembly is configured to allow said removable outer cap and said removable inner cap to be fixedly connectable to each other such that the removable outer cap is prevented of being movable with respect to the removable inner cap only when the medicament delivery device is held in a substantially vertical position such that both said removable outer cap and said removable inner cap can be removed from the cap assembly. Preferably, the removable outer 12 cap and the removable inner 16 cap are movably connected in relation to each other such that the removable outer cap is prevented of being longitudinally displaceable but rotatable with respect to the removable inner cap and wherein the cap assembly is configured to allow said removable outer cap and removable inner cap to be fixedly connectable to each other such that the removable outer cap is prevented of being rotatable with respect to the removable inner cap only when the medicament delivery device is held in a substantially vertical position such that both said removable outer cap and said removable inner cap can be removed from the cap assembly.

The cap assembly further comprises, among other elements, a retainer member 14 connectable to the medicament delivery device, a shield front 17 connectable to the medicament delivery device, said shield front being coaxially movable in relation to the retainer member, a hub 26 comprising a needle 30 having a proximal end and a distal end, said hub being coaxially movable within the retainer member, the removable inner cap 16 interactively connected to the hub 26 and to the retainer member 14, a biased clutch sleeve 46 coaxially and movable arranged between said inner and outer caps and being releasibly connectable to both said inner and outer caps, a biased outer cap locking means 18 coaxially arranged between the outer cap and the clutch sleeve and movable between a disconnected position in which the biased outer cap locking means is disconnected from both the outer cap and the clutch sleeve and a connected position in which the biased outer cap locking means is connected to both the outer cap and the clutch sleeve, and a clutch sleeve locking member 60 arranged between the clutch sleeve and the outer cap and movable between a blocking position in which the clutch sleeve locking member is connected to both the clutch sleeve and the outer cap for preventing the clutch sleeve to be moved in relation to said inner and outer caps and an unblocking position in which the clutch sleeve locking member is disconnected from both the clutch sleeve and the outer cap for allowing the clutch sleeve to be moved in relation to the inner and outer caps.

Figure 6:
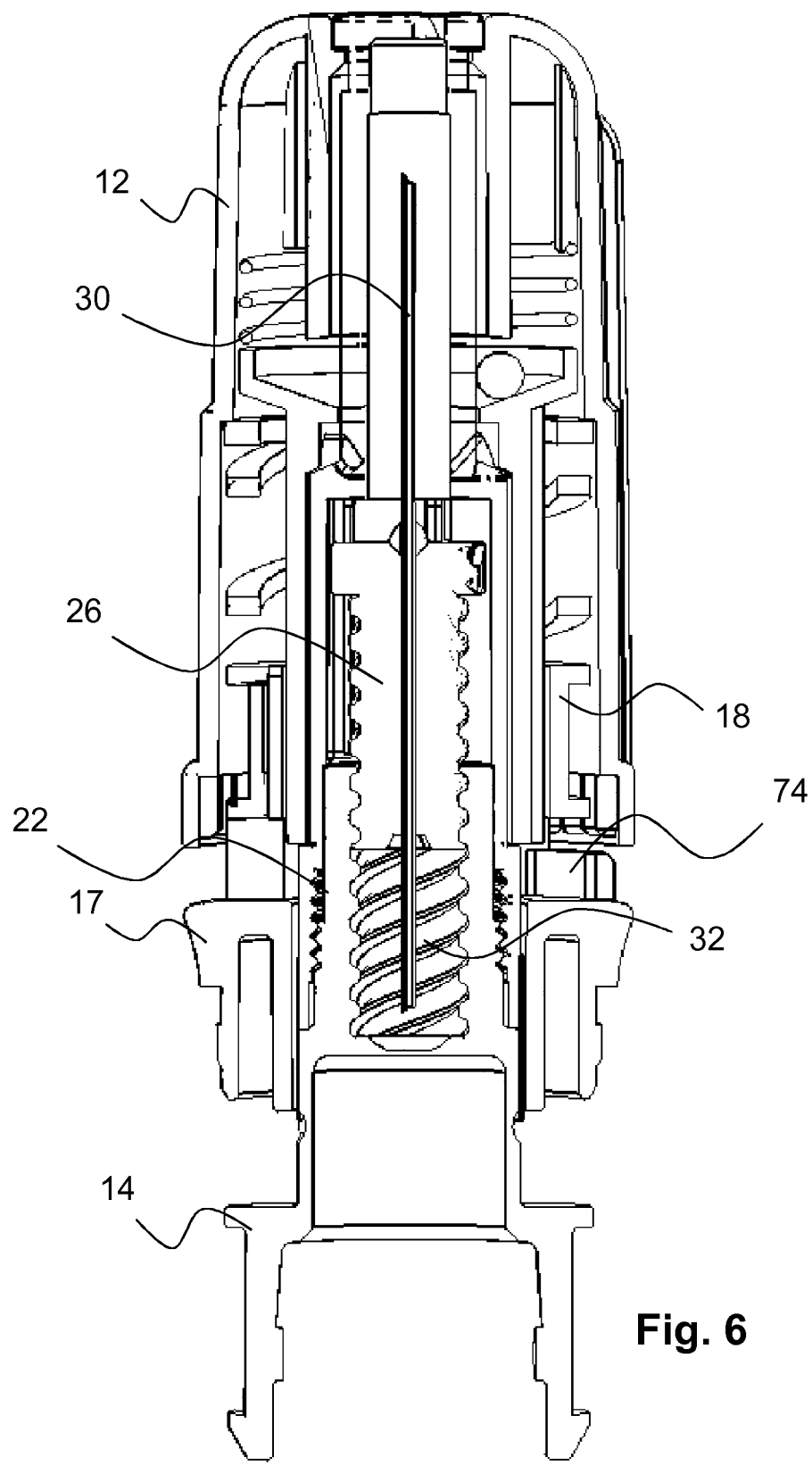
FIG. 6 is a cross-sectional side view of the cap assembly of FIG. 1 in an initial state.

The retainer member 14 is further arranged with an outer thread structure 22, FIG. 6, provided with threads that have a certain pitch. This thread structure is arranged to interact with corresponding thread structure 24 on an inner distal cylindrical surface of the inner cap 16, FIG. 4.

Inside the inner cap 16, the hub 26 is arranged, FIG. 2. The hub 26 is provided with an engagement member 28 on its outer surface, in the shown embodiment as threads. The injection needle 30 is attached to the hub 26 and longitudinally extending through it. The engagement member 28 of the hub 26 is intended to cooperate with a corresponding engagement member 32, FIG. 6, on an inner cylindrical surface of the retainer member 14, in the embodiment shown corresponding threads. The threads 28 of the hub 26 and the corresponding threads 32 on the retainer member 14 have a pitch and direction on the threads that are opposite in relation to the threads 22 of the retainer member 14 and the threads 24 on the inner cap 16, as will be explained below. The hub 26 is further arranged with longitudinally extending slits 34, FIG. 2, which slits 34 are designed to cooperate with longitudinally extending ribs 36, FIG. 4, on the inner surface of the inner cap 16, such that the hub 26 is rotationally locked, but slidable, in relation to the inner cap 16.

Figure 5:
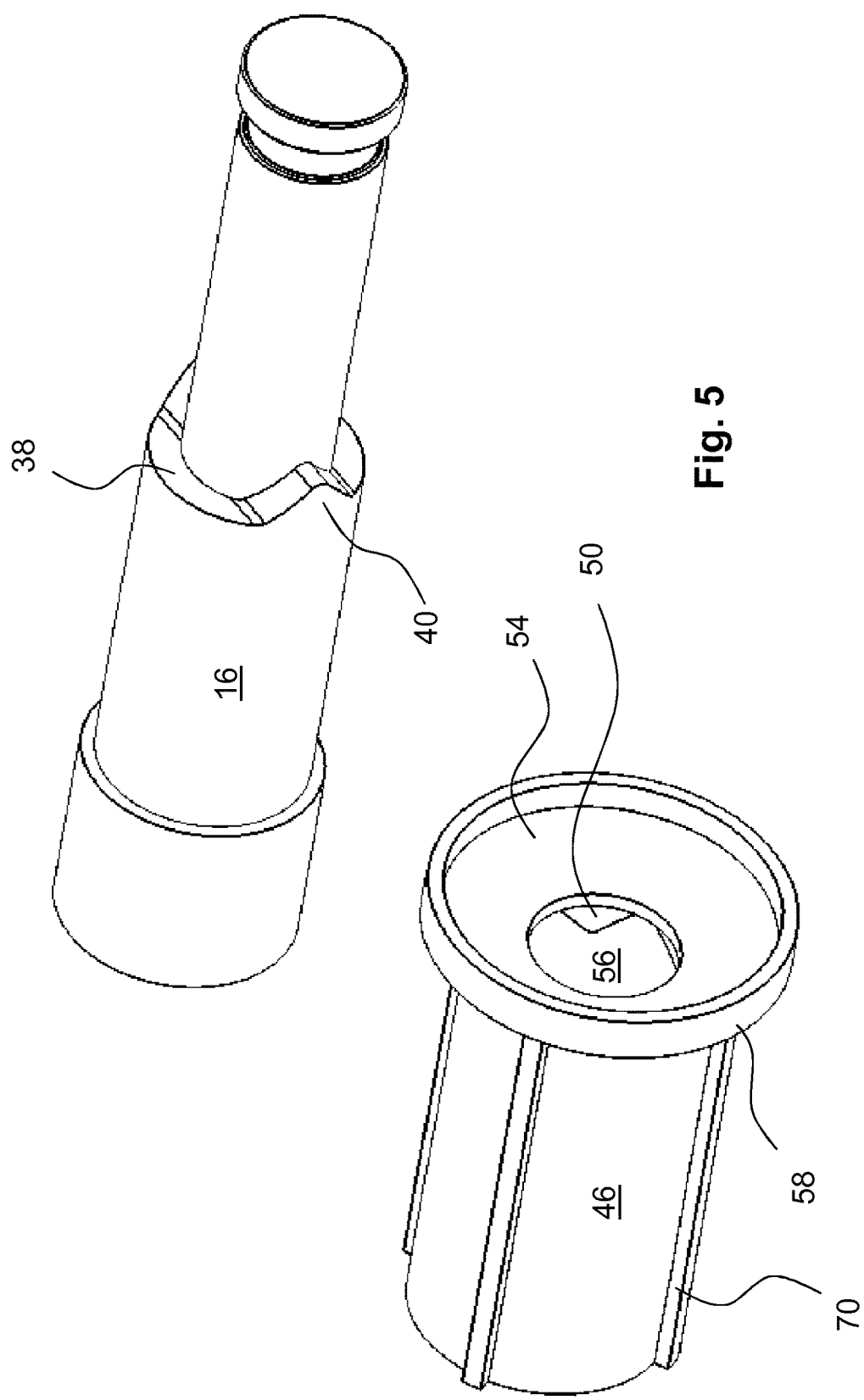

The outer surface of the inner cap 16 is arranged with a camming surface 38 on a proximally directed circumferential ledge 40, FIG. 5.

Figure 4:
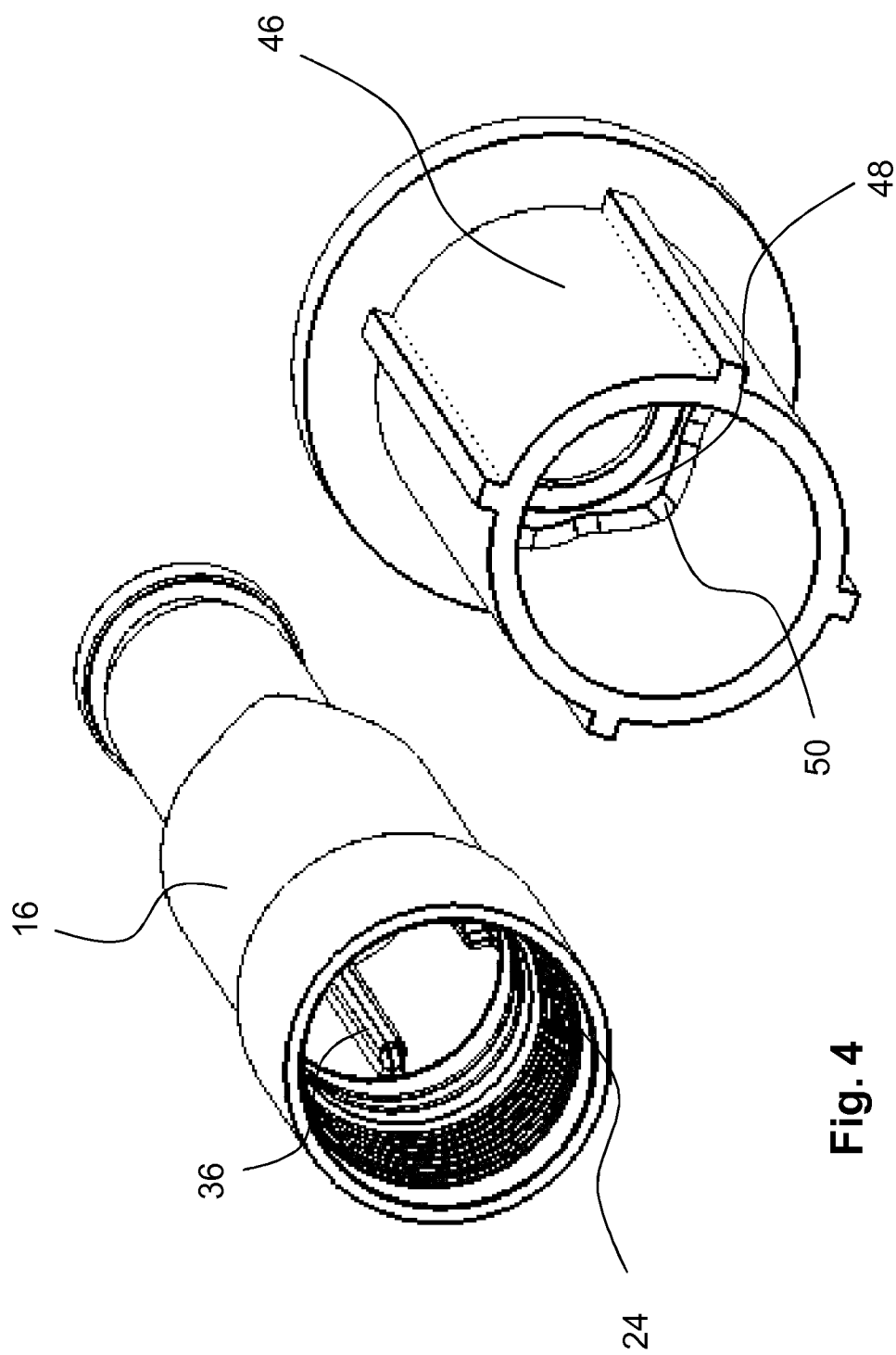

An inner surface of the clutch sleeve is arranged with camming surface 50 on a distally directed circumferential ledge 48, FIG. 4. Said camming surfaces 38, 50 being configured to interact with each other, as will be described in detail below.

The clutch sleeve 46 comprises at its proximal end a cup shaped member 54, FIG. 5, having a central opening 56 through which a proximal part of the inner cap 16 extends. The cup shaped member comprises a conical surface arranged such that it is inclined towards the opening 56. A circumferential sidewall 58 is arranged at the edge of the cup shaped member 54.

The clutch sleeve locking member 60, FIG. 2, is movable arranged in the cup shaped member, the function of which will be described below.

The outer cap 12 is arranged with a generally tubular shape having a proximal end wall 62, FIG. 2. The end wall 62 is arranged with a central opening 64 in which the proximal end of the inner cap 16 can be positioned such that the outer cap is prevented of being longitudinally displaceable with respect to the inner cap. The outer cap 12 further comprises a coaxial tubular blocking member 66 which extends longitudinally a certain length from the proximal end wall 62 towards the distal end of the device and through which the proximal part of the inner cap 16 extends, FIG. 3.

Further, a resilient member 68, FIG. 2, is arranged is arranged surrounding the coaxial tubular blocking member 66 and between a circumferential ledge surface of the cup shaped member and a support surface(s) on the inner surface of the outer cap for biasing the clutch sleeve 46.

The outer surface of the clutch sleeve 46 is arranged with a number of longitudinally extending ribs 70, FIG. 5. These ribs 70 are intended to cooperate with longitudinally extending grooves 72, FIG. 3, on an inner surface of the biased outer cap locking means 18 whereby a rotational lock is obtained but providing a longitudinal movement between the two. The biased outer cap locking means 18 is further provided with first engagement members that in the embodiment shown comprise generally circumferentially extending arms 74, FIG. 3. The arms are arranged flexible in a generally radial direction. The outer ends of the arms 74 are arranged with radially outwardly extending protrusions 76, FIG. 3, where the protrusions 76 have a generally wedge-shape as seen in a proximal or distal direction. The protrusions 76 are arranged to cooperate with a ratchet 78, FIG. 3, arranged on an inner surface of the outer cap 12 at its distal area. The teeth of the ratchet 78 preferably have shapes that form a wedge-shape as seen from the distal direction. The protrusions 76 and the ratchet 78 are thus intended to cooperate such that the outer cap 12 can only bring the biased outer cap locking means 18 with it in one direction for removal of the cap assembly. In the opposite direction, the ratchet 78 will slide over the protrusions 76, whereby the latter will flex in the radial direction due to the arms 74.

Figure 3:
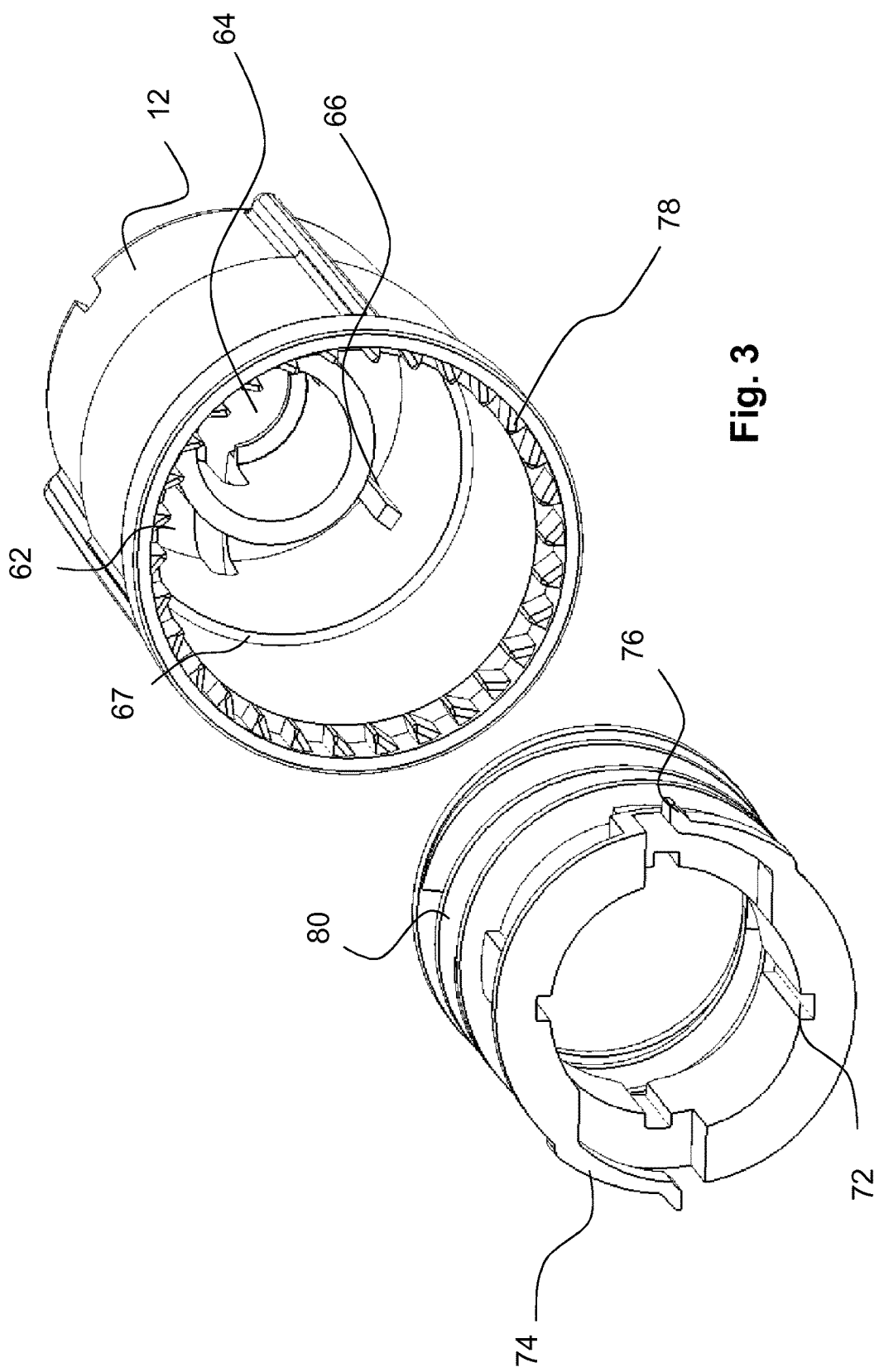
FIGS. 3-5 show detailed views of components comprised in the non-limiting example of the cap assembly vice of FIG. 1.

The biased outer cap locking means 1818 is connected to or integral with a clutch biasing means 80, FIG. 3. Said clutch biasing means 80 has a proximal end surface that rests on a circumferential ledge 67 on the inner surface of the outer cap 12, FIG. 3, and is capable of biasing the biased outer cap locking means 18 for keeping it in the disconnected position. The clutch biasing means 80 is a resilient member, preferably integrally to the biased outer cap locking means 18. The function of the clutch biasing means is to return the biased outer cap locking means 18 to the disconnected position if the cap assembly has been exposed to a sudden external force, such as if e.g. the medicament delivery device was dropped with its proximal end on a hard surface, such as a floor, wherein due to the impact forces, the biased outer cap locking means 18 had been moved into the connected position.

When the cap assembly is assembled as seen in FIG. 6, the biased outer cap locking means 18 is in the disconnected position in which said biased outer cap locking means 18 is disconnected from the outer cap 12 and from the inner cap 16 such that the outer cap 12 is rotatable in relation to said inner cap 16, i.e. the ratchet 78 of the outer cap 12 is out of engagement with the arms 74 with their protrusions 76 of biased outer cap locking means 18 since the clutch biasing means 80 is urging the biased outer cap locking means 18 in the distal direction against a proximal surface of the shield front 17.

During normal use, when a patient is to use the medicament delivery device for delivering a dose of medicament, a dose knob or the like component arranged on a medicament delivery device is manoeuvred. The medicament delivery device is of the general type disclosed in WO2011126439A1. To the extent not inconsistent with this disclosure, the disclosure of WO2011126439A1 is hereby referred to. This in turn causes an energy accumulating member to move the shield front 17 in the proximal direction. The movement of the shield front 17 in the proximal direction further causes the biased outer cap locking means 18 to be displaced in the proximal direction against the force of the clutch biasing means 80. I.e. the biased outer cap locking means 18 is displaced from the disconnected position to the connected position in which said biased outer cap locking means 18 is connected to the outer cap 12 and to the clutch sleeve 46 such that the outer cap is rotationally locked to the clutch sleeve 46.

Figure 7:
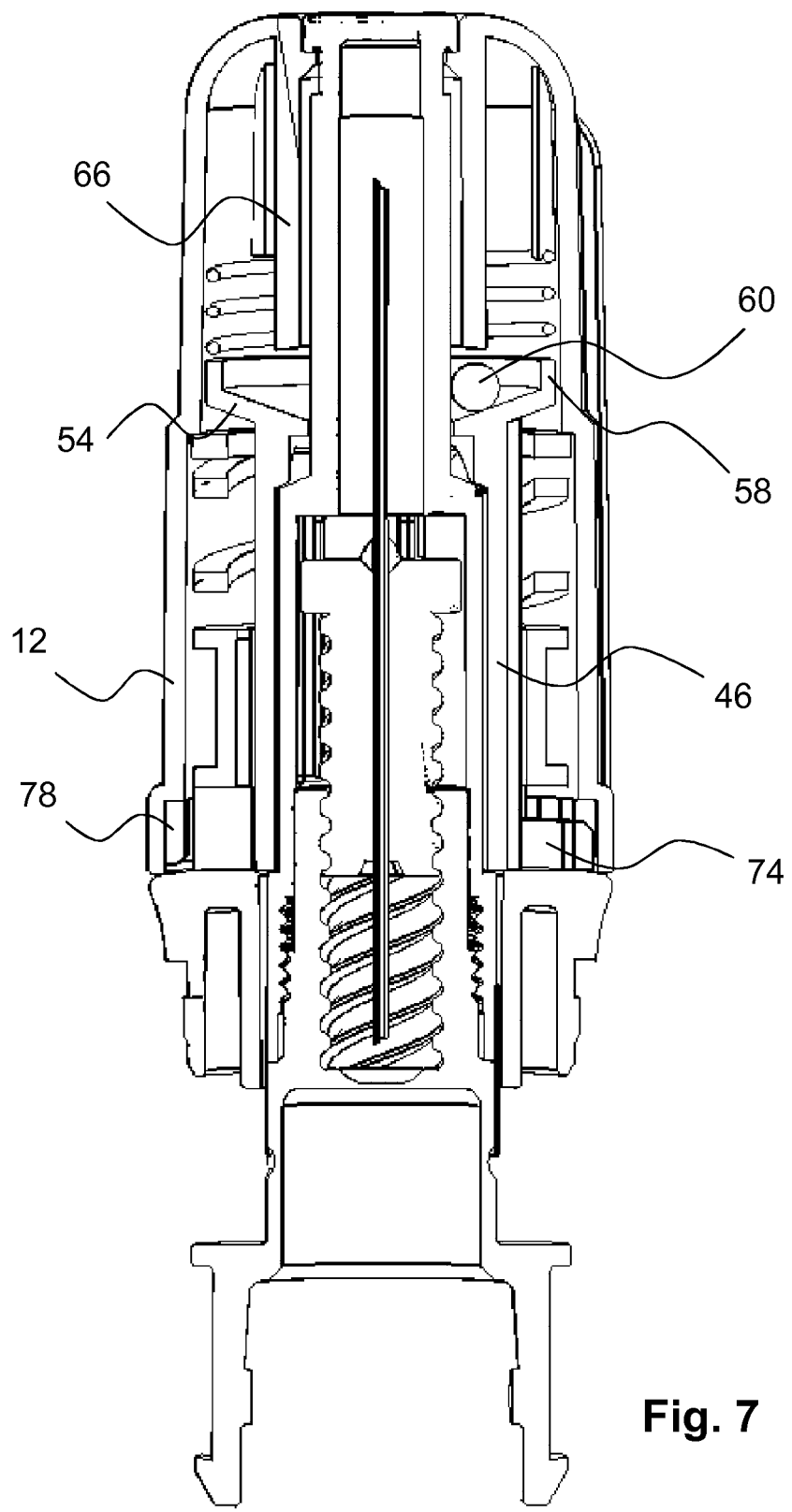
FIG. 7 is a cross-sectional side view of the cap assembly of FIG. 1 in an activated state.
Figure 8:
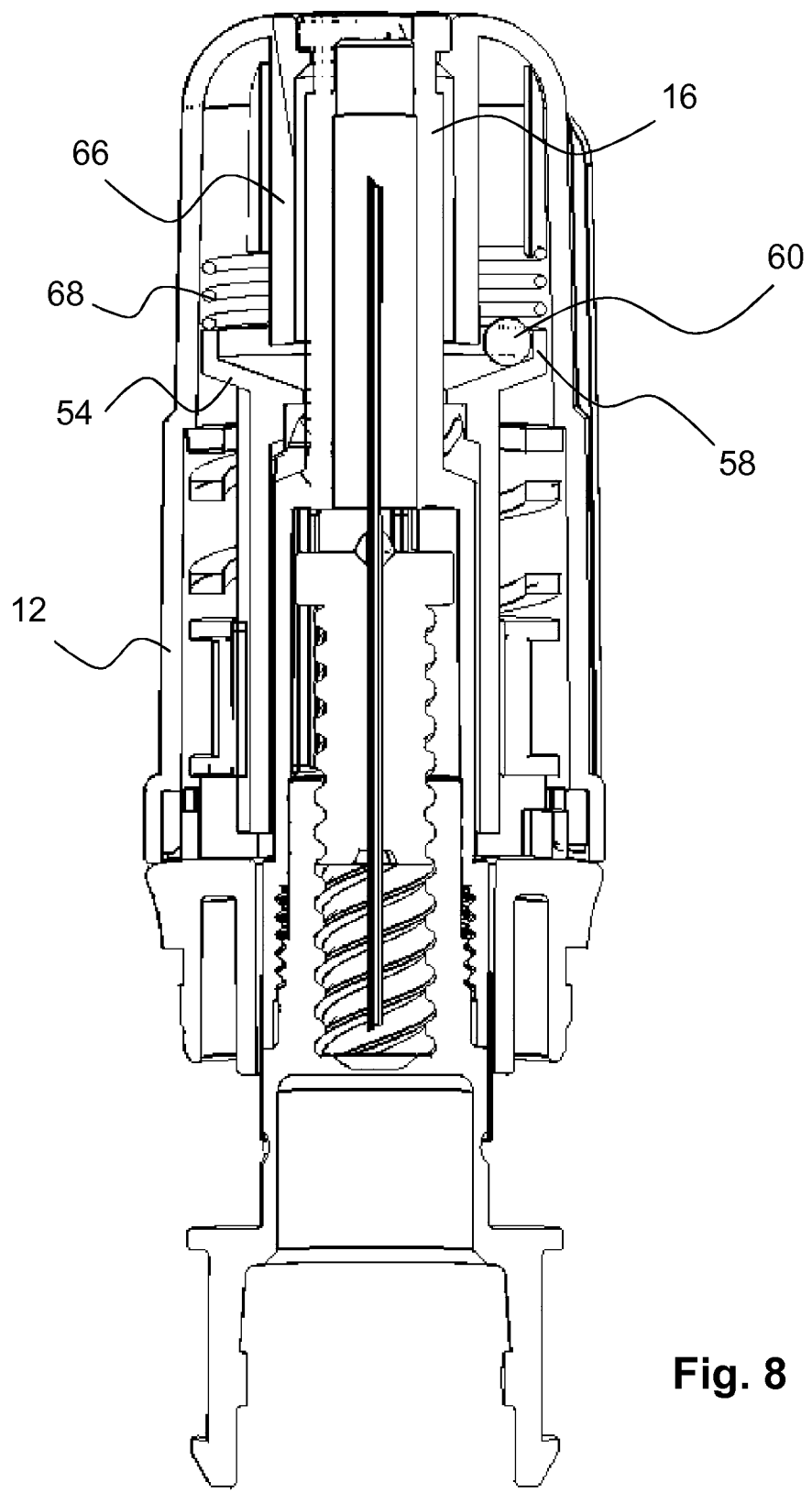
FIG. 8 is a cross-sectional side view of the cap assembly of FIG. 1 when the device is not held in the proper prescribed direction.
Figure 9:
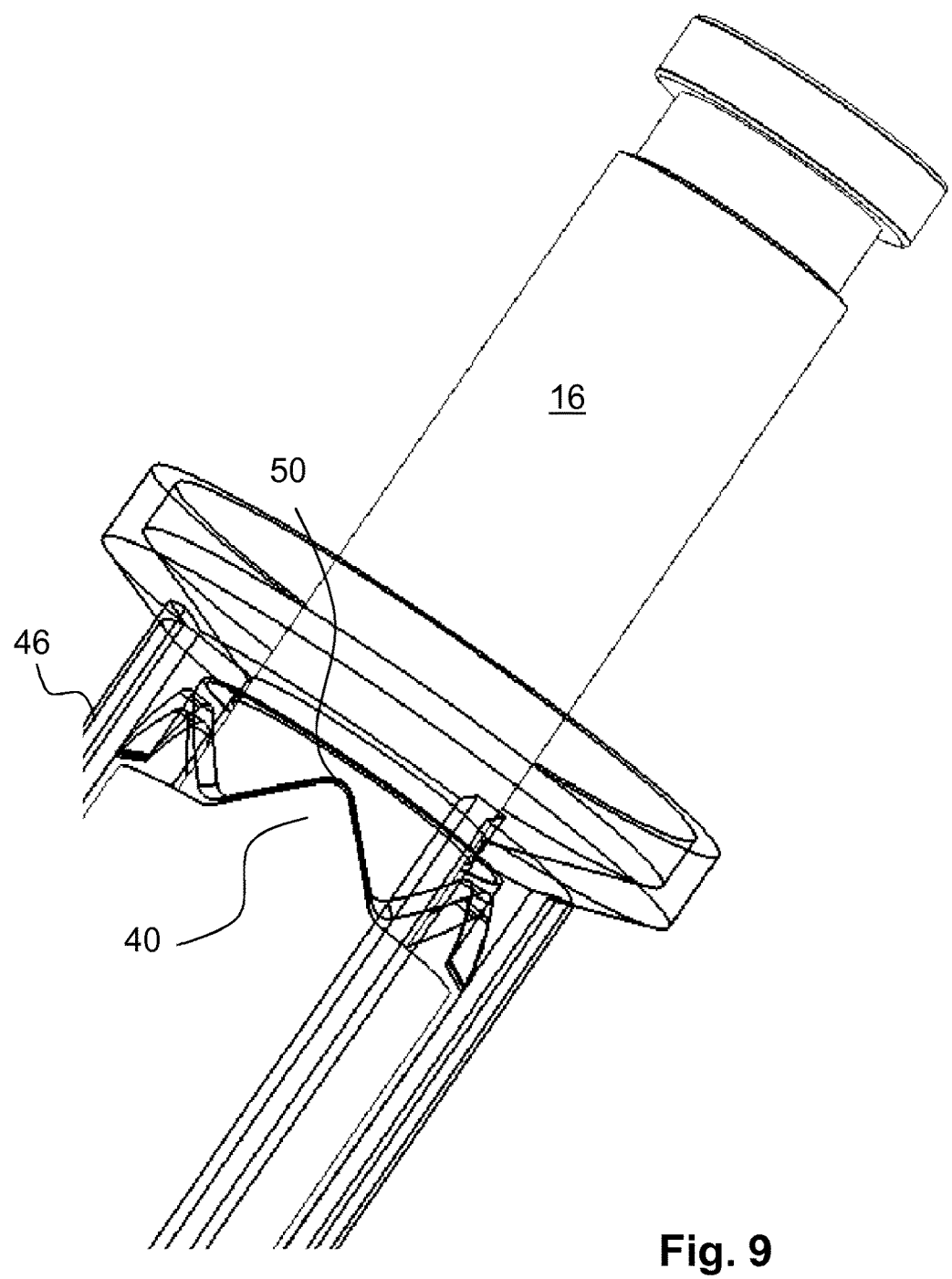
FIGS. 9-10 detailed side views of the embodiment of FIG. 1 during different operational steps.

After the displacement of the biased outer cap locking means 18 is completed, the arms 74 with the protrusions 76 and the ratchet 78 are in contact with each other, FIG. 7. According to the invention, the medicament delivery device has to be held in a substantially vertical position with the proximal end of the medicament delivery device pointing upwards when the caps are to be removed. Thus, when the medicament delivery device is held in the appropriate position, the clutch sleeve locking member 60 is urged towards the centre of the cup shaped member 54 due to its inclined surface and is resting against the inner cap 16, as shown in FIG. 7. When now the user turns the outer cap in the appropriate direction the ratchet 78 engage with the protrusions of the arms 74 so that the biased outer cap locking means 18 is also rotated. Due to the rotational lock between the biased outer cap locking means 18 and the clutch sleeve 46, the clutch sleeve will also rotate. Also, when now the user turns the outer cap, the camming surface of the clutch sleeve 46 interacts with the camming surface of the inner cap 16 such that the clutch sleeve will try to be longitudinally displaced in relation to the inner cap against the bias of the resilient member 68, FIG. 9. This longitudinally displacement of the clutch sleeve is however prevented because the clutch sleeve locking member 60 is in the blocking position. Since the clutch sleeve locking member 60 is at its innermost position in contact with the inner cap 16, as seen in FIG. 7, because the user is holding the medicament delivery device substantially vertical and due to the inclination of the conical surface of the he cup shaped member, clutch sleeve locking member 60 will be moved in contact with the blocking member 66 of the outer cap 12, whereby displacement of the clutch sleeve 46 in the longitudinal direction is prevented. Thus the inner cap 16 will rotate together with the clutch sleeve.

In turn, because the inner cap 16 is rotatably connected to the hub 26, the hub 26 will also rotate, causing it to be screwed distally into the retainer member 14 whereby the pointed distal end of the needle 30 can penetrates a sterile barrier and subsequently the membrane of a medicament container (not shown). Finally, the outer cap 12 and the inner cap 16 can be removed. Any over-pressure inside the medicament container will now be removed through the injection needle and due to the proper position of the device, only air and no medicament will be expelled.

Figure 10:
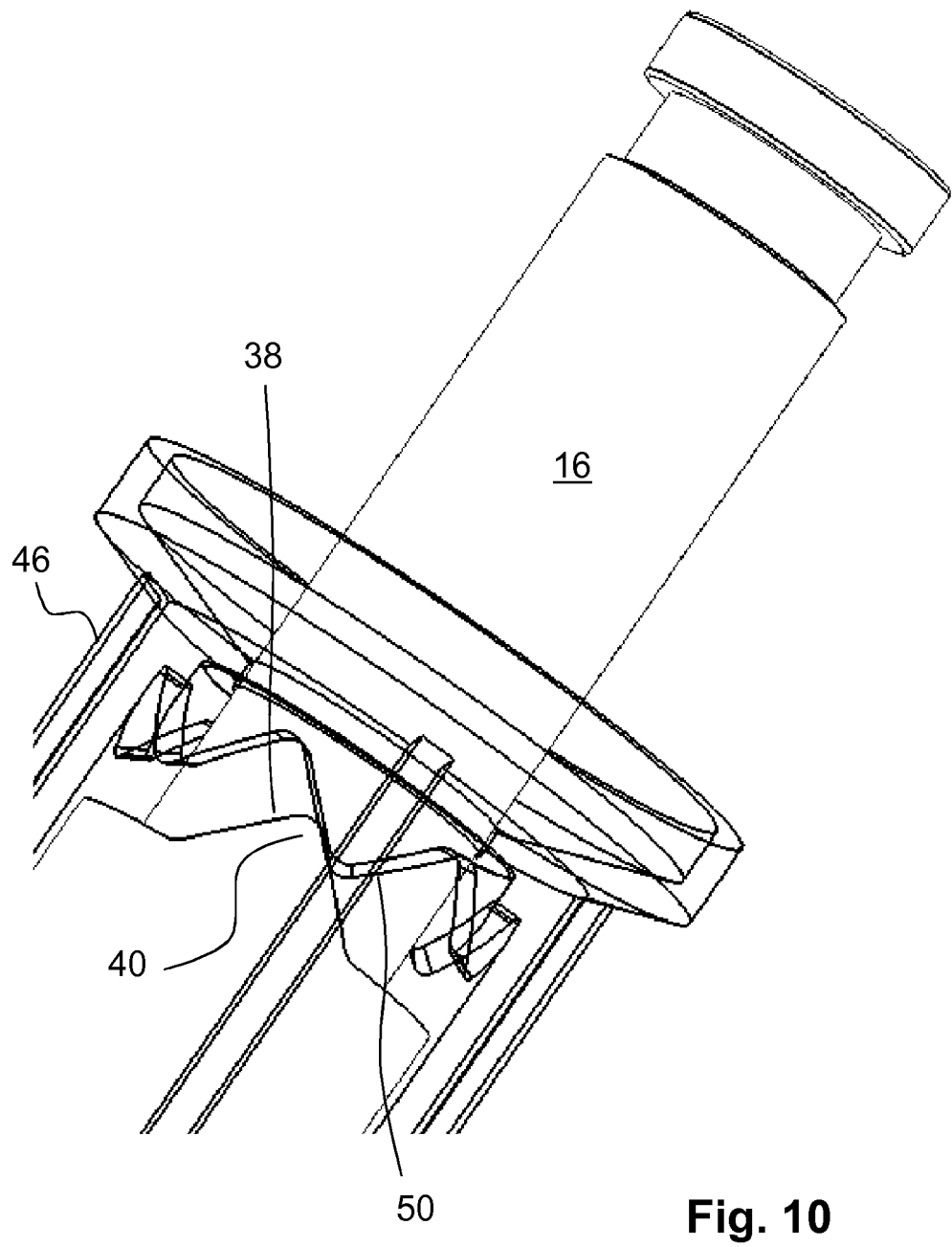

If however the user does not hold the medicament delivery device properly in a generally vertical position, but tilts the device more than is allowed, then the clutch sleeve locking member 60 will move out of its innermost position, i.e. from the blocking to the unblocking position. If the user now turns the outer cap 12, the clutch sleeve 46 will be longitudinally displaced against the bias of the resilient member 68 as described above. However, since the clutch sleeve locking member 60 is in the unblocking position, longitudinal displacement of the clutch sleeve 46 against the bias of the resilient member 68 in relation to the inner cap 16 is not prevented and the camming surface of the clutch sleeve 46 will ride over the camming surface of the inner cap 16, FIG. 10. Thus, rotation of the outer cap 12 and the clutch sleeve 46 will not cause any rotation of the inner cap 16, whereby any removal of the caps when the medicament delivery device is not held in the proper position is prevented.

It is to be understood that the embodiment described above and shown in the drawings is to be regarded only as a non-limiting example of the invention and that it may be modified in many ways within the scope of the patent claims.

The invention claimed is:

1. A cap assembly configured to connect to a medicament delivery device having a distal end and a proximal end, comprising:
   a removable outer cap and a removable inner cap movably connected in relation to each other;
   a clutch sleeve coaxially arranged with the removable inner and outer caps and operably connected to the removable outer cap; and
   a clutch sleeve locking member disposed between the clutch sleeve and the removable outer cap and movable between an unblocking position and a blocking position, in which blocking position the clutch sleeve is locked with the removable inner cap, the clutch sleeve locking member being movable from the unblocking position to the blocking position only when the cap assembly is held in a substantially vertical position;
   wherein the removable outer cap and the removable inner cap are movably connected in relation to each other such that longitudinal displacement of the removable outer cap is prevented but the removable outer cap is rotatable with respect to the removable inner cap, and the removable outer cap and the removable inner cap are configured to fixedly connect to each other such that the removable outer cap is not rotatable with respect to the removable inner cap only when the medicament delivery device is held in a substantially vertical position.

2. The cap assembly of claim 1, wherein the outer cap comprises a proximal end wall having a central opening, in which a proximal end of the inner cap is positioned such that the outer cap is prevented from longitudinal displacement but is rotatable with respect to the inner cap.

3. The cap assembly of claim 2, wherein the outer cap further comprises a coaxial tubular blocking member extending longitudinally a certain length from the proximal end wall toward the distal end of the medicament delivery device and through which the proximal end of the inner cap extends.

4. The cap assembly of claim 3, wherein the clutch sleeve comprises at its proximal end a cup-shaped member having a central opening through which the proximal end of the inner cap extends.

5. The cap assembly of claim 4, further comprising a resilient member that surrounds the coaxial tubular blocking member between a circumferential ledge surface of the cup-shaped member and at least one support surface on an inner surface of the outer cap for biassing the clutch sleeve.

6. The cap assembly of claim 5, wherein the clutch sleeve locking member is movable in the cup-shaped member.

7. The cap assembly of claim 6, wherein the clutch sleeve locking member is a rolling member.

8. A cap assembly configured to connect to a medicament delivery device having a distal end and a proximal end, comprising:
   a removable outer cap and a removable inner cap movably connected in relation to each other;
   a clutch sleeve coaxially arranged with the removable inner and outer caps and operably connected to the removable outer cap;
   a clutch sleeve locking member disposed between the clutch sleeve and the removable outer cap and movable between an unblocking position and a blocking position, in which blocking position the clutch sleeve is locked with the removable inner cap, the clutch sleeve locking member being movable from the unblocking position to the blocking position only when the cap assembly is held in a substantially vertical position;
   a retainer member configured to connect to the medicament delivery device;
   a shield front configured to connect to the medicament delivery device, the shield front being coaxially movable in relation to the retainer member;
   a hub, comprising a needle having a proximal end and a distal end, the hub being coaxially movable within the retainer member, and the removable inner cap being interactively connected to the hub and to the retainer member; and
   a biassed outer cap lock coaxially disposed between the removable outer cap and the clutch sleeve and movable between a disconnected position, in which the biassed outer cap lock is disconnected from both the outer cap and the clutch sleeve, and a connected position, in which the biassed outer cap lock is connected to both the outer cap and the clutch sleeve;
   wherein in the unblocking position, the clutch sleeve locking member is disconnected from both the clutch sleeve and the outer cap to allow the clutch sleeve to move in relation to the inner and outer caps.

9. The cap assembly of claim 8, wherein the removable outer cap is biased to disconnect from the clutch sleeve such that the outer cap rotates with respect to the clutch sleeve only when the biased outer cap lock is in the disconnected position and the clutch sleeve locking member is in either the blocking position or the unblocking position.

10. The cap assembly of claim 9, wherein the removable outer cap is configured to connect to the clutch sleeve such that the outer cap and the clutch sleeve rotate with respect to the inner cap only when the biassed outer cap lock is in the connected position and the clutch sleeve locking member is in the unblocking position.

11. The cap assembly of claim 10, wherein the clutch sleeve and the removable inner cap are configured to connect to each other such that the clutch sleeve is neither rotatable nor longitudinally displaceable with respect to the removable inner cap only when the clutch sleeve locking member is in the blocking position and the biassed outer cap lock is in the connected position.

12. The cap assembly of claim 11, wherein the outer and inner caps are configured to connect to each other through the clutch sleeve such that movement of the outer cap is transferred to the inner cap only when the clutch sleeve locking member is in the blocking position and the biassed outer cap lock is in the connected position.

13. A cap assembly configured to connect to a medicament delivery device having a distal end and a proximal end, comprising:
- a removable outer cap and a removable inner cap movably connected in relation to each other;
- a clutch sleeve coaxially arranged with the removable inner and outer caps and operably connected to the removable outer cap; and
- a clutch sleeve locking member disposed between the clutch sleeve and the removable outer cap and movable between an unblocking position and a blocking position, in which blocking position the clutch sleeve is locked with the removable inner cap, the clutch sleeve locking member being movable from the unblocking position to the blocking position only when the cap assembly is held in a substantially vertical position;
- wherein the clutch sleeve comprises a cam surface and the inner cap comprises a corresponding cam surface, the cam surfaces being configured to interact with each other; when the clutch sleeve locking member is in the blocking position and the biassed outer cap lock is in the connected position, the cam surfaces are rotationally locked, whereby rotation of the outer cap causes rotation of the inner cap; and when the clutch sleeve locking member is in the unblocking position and the biassed outer cap lock is in the connected position, the cam surfaces are rotationally unlocked, whereby rotation of the outer cap causes a rotation and a longitudinal displacement of the clutch sleeve in relation to the inner cap.

* * * * *